(12) United States Patent
Hidle et al.

(10) Patent No.: US 6,910,822 B2
(45) Date of Patent: Jun. 28, 2005

(54) ANTISEPTIC PREOPERATIVE APPLICATOR

(75) Inventors: Rex A. Hidle, San Antonio, TX (US);
Shawn B. Gentry, Fort Worth, TX (US); H. Paul Dorman, Fort Worth, TX (US)

(73) Assignee: Healthpoint, Ltd., Fort Worth, TX (US)

( * ) Notice: Subject to any disclaimer, the term of this patent is extended or adjusted under 35 U.S.C. 154(b) by 0 days.

(21) Appl. No.: 10/294,289

(22) Filed: Nov. 14, 2002

(65) Prior Publication Data

US 2003/0068190 A1 Apr. 10, 2003

Related U.S. Application Data

(63) Continuation of application No. 09/934,142, filed on Aug. 21, 2001, now Pat. No. 6,505,985.

(51) Int. Cl.⁷ .................................. B43K 5/14
(52) U.S. Cl. ................ 401/134; 401/133; 604/2; 604/3
(58) Field of Search ............... 401/132–134; 604/1–3

(56) References Cited

U.S. PATENT DOCUMENTS

| | | | | |
|---|---|---|---|---|
| 2,240,604 A | * | 5/1941 | Berger | 401/134 |
| 3,481,676 A | * | 12/1969 | Schwartzman | 401/134 |
| 4,507,111 A | * | 3/1985 | Gordon et al. | 401/134 |
| 5,342,136 A | * | 8/1994 | Fukami | 401/134 |
| 5,769,552 A | | 6/1998 | Kelley | |
| 5,791,801 A | | 8/1998 | Miller | |

OTHER PUBLICATIONS

Allegiance Healthcare Corporation, One–Step Fluid–Resistant Prep Solution, Allegiance a Cardinal Health Company, Copyright 2000, Allegiance Healthcare Corporation (Prevail–Fx is a trademark of Allegiance Healthcare Corporation).

* cited by examiner

Primary Examiner—David J. Walczak
(74) Attorney, Agent, or Firm—McKee, Voorhees & Sease, P.L.C.

(57) ABSTRACT

A liquid dispenser applicator for preoperative preparation of a target area of a patient's skin is comprised of two integrated components, a handle portion and a canister vessel. The two components are locked by a locking and sealing ring mechanism to prevent accidental rupture of the sterile antiseptic fluid in the canister vessel. When the lock is unlocked, the unit contains a perforator designed to initially slit the membrane followed by pushing it open further and thereafter venting it to provide dual-staged self-venting by the perforator for ease of flow.

12 Claims, 2 Drawing Sheets

ANTISEPTIC PREOPERATIVE APPLICATOR

This application is a continuation of 09/934,142, now U.S. Pat. No. 6,505,985 filed on Aug. 21, 2001.

FIELD OF THE INVENTION

This invention relates to liquid applicators, and more particularly, to applicators for preparing a portion of a person's body with antiseptic fluid, often used just before surgery.

BACKGROUND OF THE INVENTION

Preparing a person for surgery is commonly called "prepping". It is typical to scrub the target body portion of the patient with an antiseptic solution. Antiseptic solutions are typically dispensed from a vessel. It is necessary for that vessel to be sterile and sealed prior to use. Commonly employed applicators use an ampoule containing the antiseptic liquid. The ampoule is broken just prior to application. A typical example of such an applicator is that disclosed in U.S. Pat. No. 5,791,801. The problem with such applicators is that they require breaking of the tip of the ampoule to release antiseptic fluid. The attendant consequences of having broken ampoule glass are risk of damage to the dispenser allowing glass to contact the patient, risking injury, clogging, and poor flow to the applicator pad or sponge.

In order to overcome this problem, dispensers have been designed which use sealing membranes as opposed to an ampoule. However, the problem with current dispensers that use sealing membranes is that the membranes are often subject to accidental rupture resulting in flow of the antiseptic fluid when it is not desired. This is wasteful. One solution to this problem of accidental or unwanted activation of the dispenser system is expressed in U.S. Pat. No. 5,769,552. However, the solution to the problem expressed in this patent is complex, and high in expense to manufacture.

It can be seen therefore that there is a real and continuing need for a liquid applicator/dispenser used for pre and post operative preparation which is easy of manufacture, durable in use, cost effective and one which has minimized risk of accidental rupture of the sealing membrane. This invention has as its primary objective the fulfillment of each of these real and continuing needs.

SUMMARY OF THE INVENTION

This invention provides an improved antiseptic applicator useful in patient preparation for surgery. It is an applicator designed for easy dispensation of fluid and yet one which is designed to avoid accidental discharge. At the same time it avoids the necessity of using ampoules. In particular, by employing two integrated components (handle and canister) which cooperate to achieve a product dispensing system, and by retaining these two components by a locking and sealing ring, locking screw and or cam-locking mechanism, the desired product is retained, premature rupture avoided and a unique but simple fluid product holding and dispensing system is realized. In one version of the present invention, the fluid product holding and dispensing system possesses two separate and distinct lock positions, which assures that the system is retained in its locked position, until change is desired by the user. As a result, accidental or unwanted activation of the system is eliminated and users are assured that the product retained and sealed in the container remains sterile and sealed until use is desired. Accidental opening or rupturing of the vessel seal is eliminated. The puncture apparatus for the seal is dual staged and self-venting. The first stage punctures and cuts the membrane seal and then begins to press the membrane/seal back onto the inside of the liquid holding canister. At this point, the second stage of the puncture apparatus contacts the membrane/seal and further opens the previously cut area, thus enlarging the initial opening substantially while causing the membrane/seal to be laid further back into the liquid holding canister. Around the outside of the dual staged puncturing mechanism are vents, which aid airflow into the liquid holding canister. In addition, a flap seal and or form/fill/seal mechanism/membrane could be used to manufacture and seal the canister member of this dispensing system. Finally, by employing the two-component fluid product holding and dispensing trigger assembly of this invention, an easily manufactured, reasonably priced system is attained which is capable of providing consistent, dependable, repeatable results.

While the invention will next be described in connection with certain embodiments, there is no intent to limit it to those embodiments. On the contrary, the intent is to cover all the alternatives, modifications, and equivalents included within the spirit and scope of the invention as defined by the written description and the claims.

While the reference in the description given below is to the specific use in the environment of preoperative antiseptic fluids, it should be understood that this container has uses beyond this with respect to application environments. For example, it may be used with many different topical liquids, gels, creams, lotions, ointments or other solutions and suspensions. Specific examples might include anti-inflammatories, antifungals, antibacterials, cosmetics, analgesics, etc.

DETAILED DESCRIPTION OF THE PREFERRED EMBODIMENT

Figure 8:
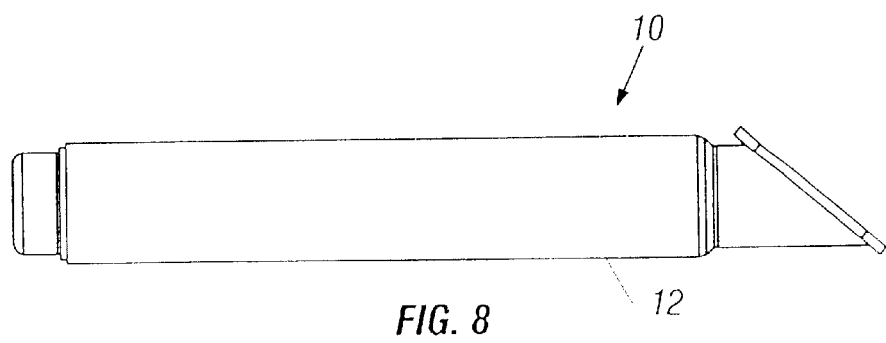
FIG. 8 is an elevated side view of the liquid dispenser.
Figure 1:
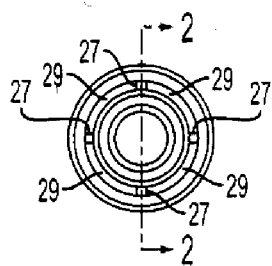
Figure 2:
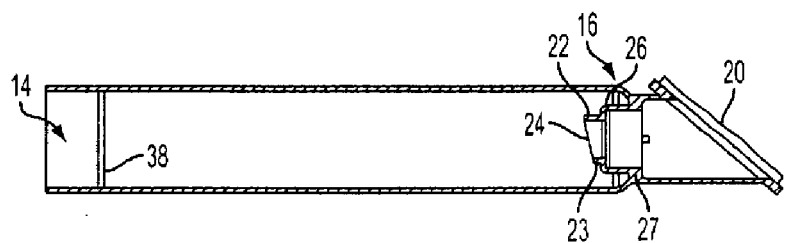
Figure 3:
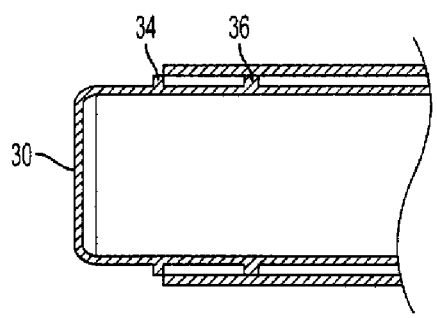
Figure 4:
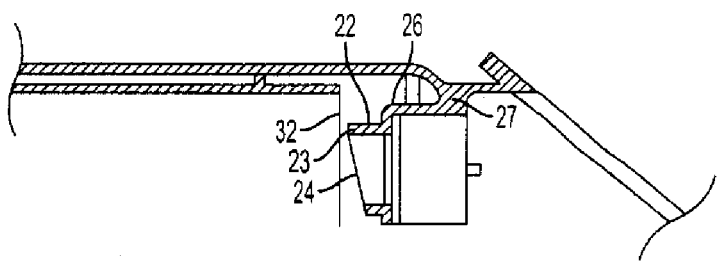

Turning now to the drawings and particularly to FIG. 8, there is shown an applicator 10 of the present invention. Applicator 10 has a handle portion housing 12 (see FIG. 2) of generally cylindrical configuration. It has a first end 14 and a second end 16. The first end 14 is open exposing the interior of the handle portion. The second end 16 terminates in a neck which at its end has an applicator pad 20 for applying liquid antiseptic. Internally mounted as an integral part of the handle portion housing 12 is a perforator 22 which has a sufficiently sharp edge 23 to allow it to rupture sealed membranes when it pushes against them. Perforator 22 has two stages, a first stage 24 which punctures a sealing membrane and when pushed further against the membrane, the second stage 26 further opens the previously cut area of the membrane 32, thus enlarging the initial hole and causing the membrane seal 32 to be laid further back into the liquid canister 28. The perforator 22 is thus a dual stage puncturing mechanism. Initially it slits a hole in any membrane 32, then spreads it wider and protrusions 27 provide a plurality of vents 29 to aid airflow. Protrusions 27 attach perforator 24 to handle portion 12.

Canister 28 is cylindrical and adapted for telescopic movable fitting relationship within the first end 14 of the handle portion 12. It has a closed rear end 30 and a front end 31 with a sealed membrane 32 across it. Canister 28 is capable of sliding movement within the internal cylindrical wall defined by the inside of handle portion 12. Adjacent the closed rear end 30 of canister 28 are a pair of lock rings. Lock ring 34 can be characterized as a stop ring and ring 36 can be characterized as a seal ring. It has an angular rib edge which mates within a notch 38 in interior wall of handle portion 12. The stop ring 34 abuts up against the open first end 14 of handle portion 12.

Certain constructional features are worthy of mention in the context of the preferred embodiment. Ideally the canister 28 is made of high density polyethylene and the handle portion 12 is made of low density polyethylene. In this way, the modulus of elasticity and therefore the flexibility of the handle portion is slightly greater than that of the canister portion. As a result, when a user of the system impacts the back end 30 of the canister 28 against a surface, stop ring 34 (see FIG. 3) slides inside interior wall of handle portion 12 and the canister moves forward so that seal 32 abuts initially against perforator 22. Because of the impact, the seal 32 is easily ruptured. Continued forward movement allows the shoulder or second stage 26 of the perforator to open the seal 32 even further and then protrusions 27 provide a plurality of vents 29. As a result of the dual stage rupturing, the unit is then self venting to allow better flow. The first stage 24 punctures and cuts the membrane seal 32 and then begins to press the membrane/seal back onto the inside of the liquid dispenser canister 28. At this point, the second stage 26 of the perforator 22 contacts the membrane seal and further opens the previously cut area thus enlarging the initial hole substantially and causing the membrane/seal to be laid further back into the liquid holding dispenser. Liquid contained in the canister 28 is released to flow against the pad which becomes soaked and when brushed against the surface of skin, applies the antiseptic.

Figure 3:
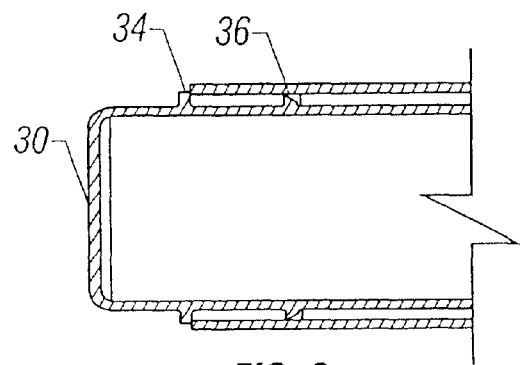
FIG. 3 is cross-sectional view in fragment of the rear end of the dispenser showing the locked position of the canister and handle.
Figure 4:
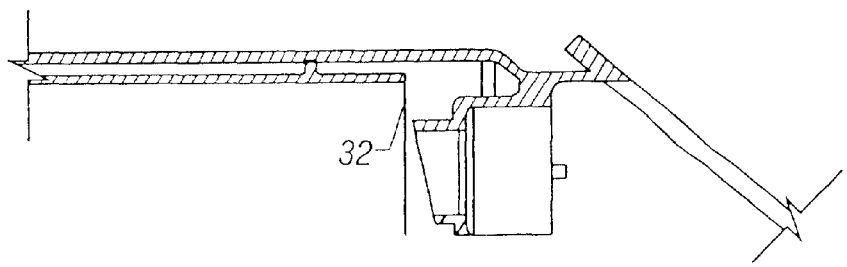
FIG. 4 is a cross-sectional view in fragment of the forward end of the dispenser showing the perforator closely adjacent the sealing membrane.
Figure 5:
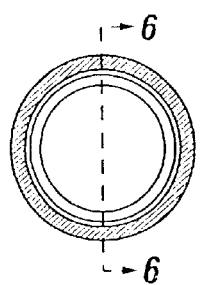
FIG. 5 is a cross-sectional view of the canister along a vertical axis.
Figure 6:
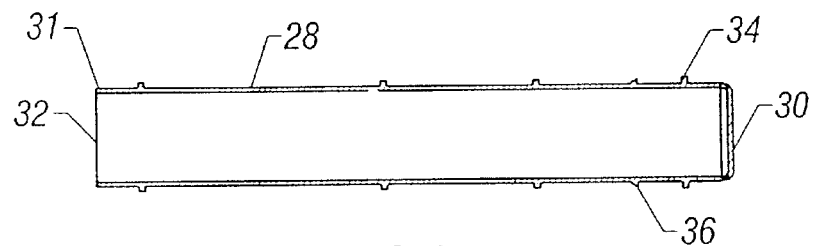
FIG. 6 is a cross-sectional of the canister along line 6—6 of FIG. 5.
Figure 7:
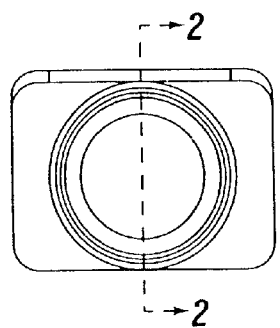
FIG. 7 is a rear end view of the canister.

In the non-use locked position, as illustrated in FIG. 3, stop ring 34 and seal ring 36 assure against inadvertent and accidental seal rupture. Even dropping of the unit will not push the canister 28 telescopically forward since it takes more impact than a simply drop to push it forward and rupture the seal.

The seal may be of conventional foil construction and the precise material used is not a critical part of the invention. For examples of suitable film forming materials, see U.S. Pat. No. 4,585,129, the disclosure of which is incorporated herein by reference to the extent that it discloses suitable foil or film formers.

From the above, it can be seen that the invention accomplishes at least all of its stated objectives.

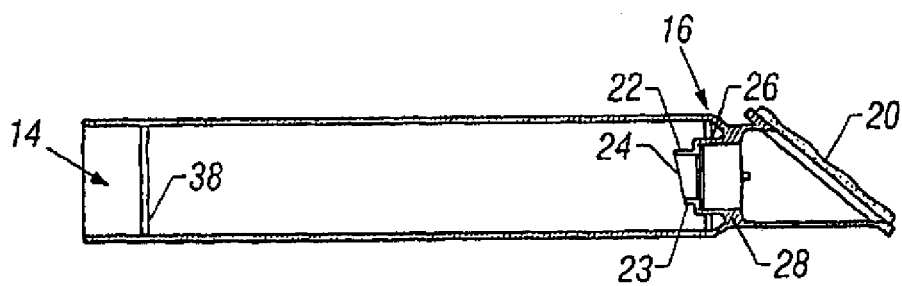

What is claimed is:

1. A liquid applicator, comprising:
   a handle portion having first and second ends, said first end having a neck terminating at a pad for applying liquid, said handle portion having a handle wall forming an elongated cavity between the first and second ends;
   a canister portion disposed within the first end of the handle portion, and having a closed rear end, a front end and a sealed membrane over said front end;
   a perforator mounted within the elongated cavity and spaced from the handle wall, the perforator adapted for puncturing the sealed membrane such that liquid released from the canister portion flows through the perforator to the pad;
   a plurality of vents positioned around the perforator between the handle wall and the perforator to allow air to flow into the canister portion after the perforator has punctured the sealed membrane.

2. The liquid applicator of claim 1 wherein the liquid is an antiseptic.

3. The liquid applicator of claim 1 wherein the canister portion includes a stop ring to prevent accidental puncture of the sealed membrane.

4. The liquid applicator of claim 1 wherein the handle portion is made of low density polyethylene and the canister portion is made of high density polyethylene.

5. The liquid applicator of claim 1 wherein the canister portion includes a sealing ring to prevent leakage of the liquid.

6. A liquid applicator, comprising:
   a handle portion having first and second ends, said first end having a neck terminating at a pad for applying liquid;
   a canister portion disposed within the first end of the handle portion and having a closed rear end, a front end and a sealed membrane over said front end;
   a perforator mounted within the handle portion, the perforator having a first stage adapted for rupturing the sealed membrane and a second stage comprising a shoulder such that continued movement of the canister portion against the perforator further opens the sealed membrane after rupturing, the perforator having an opening extending there through for permitting fluid flow through the perforator from the canister to the pad after rupturing the sealed membrane.

7. The liquid applicator of claim 6 further comprising a plurality of vents between the handle portion and the perforator to allow air to flow into the canister portion.

8. The liquid applicator of claim 6 wherein the liquid is an antiseptic.

9. The liquid applicator of claim 6 wherein the canister portion includes a stop ring to prevent accidental puncture of the sealed membrane.

10. The liquid applicator of claim 6 wherein the canister portion includes a sealing ring to prevent leakage of liquid.

11. A liquid applicator according to claim 6 wherein the vents provide for fluid flow outside the perforator from the canister to the pad after the perforator has punctured the sealed membrane.

12. A liquid applicator according to claim 1 wherein a plurality of protrusions attaching the perforator to the handle.

* * * * *

UNITED STATES PATENT AND TRADEMARK OFFICE
CERTIFICATE OF CORRECTION

PATENT NO. : 6,910,822 B2 Page 1 of 3
APPLICATION NO. : 10/294289
DATED : June 28, 2005
INVENTOR(S) : Hidle et al.

Figure 1:
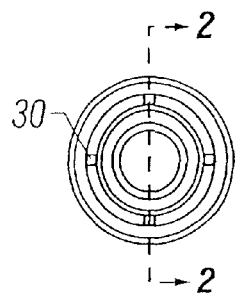
FIG. 1 is a rear end view into the handle portion looking at the perforator.
Figure 2:
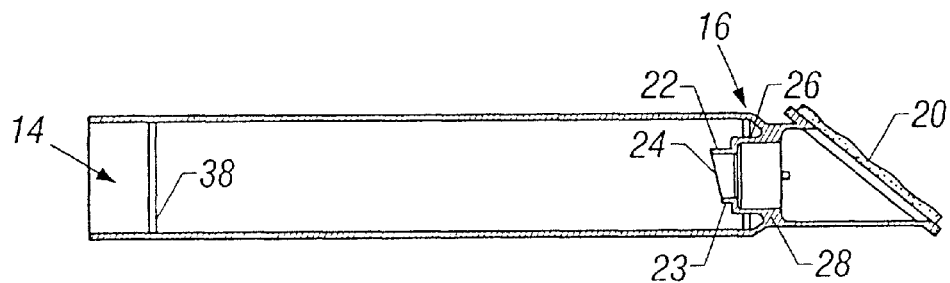
FIG. 2 is a side view of the handle portion along lines 2—2 of FIG. 1.

It is certified that error appears in the above-identified patent and that said Letters Patent is hereby corrected as shown below:

Title page, illustrative fig. 2 should be deleted and substitute therefore the attached title page consisting of the attached illustrative fig. 2.

In the Drawings

The drawing sheet 1 of 2 consisting of Fig(s) 1-4 should be deleted and substitute therefore the attached drawing sheet 1 of 2 consisting of Fig(s) 1-4.

Signed and Sealed this

Nineteenth Day of January, 2010

David J. Kappos
*Director of the United States Patent and Trademark Office*

United States Patent
Hidle et al.

(10) Patent No.: US 6,910,822 B2
(45) Date of Patent: Jun. 28, 2005

(54) ANTISEPTIC PREOPERATIVE APPLICATOR

(75) Inventors: Rex A. Hidle, San Antonio, TX (US); Shawn B. Gentry, Fort Worth, TX (US); H. Paul Dorman, Fort Worth, TX (US)

(73) Assignee: Healthpoint, Ltd., Fort Worth, TX (US)

( * ) Notice: Subject to any disclaimer, the term of this patent is extended or adjusted under 35 U.S.C. 154(b) by 0 days.

(21) Appl. No.: 10/294,289

(22) Filed: Nov. 14, 2002

(65) Prior Publication Data

US 2003/0068190 A1 Apr. 10, 2003

Related U.S. Application Data

(63) Continuation of application No. 09/934,142, filed on Aug. 21, 2001, now Pat. No. 6,505,985.

(51) Int. Cl.[7] ................................................. B43K 5/14
(52) U.S. Cl. ........................ 401/134; 401/133; 604/2; 604/3
(58) Field of Search .............................. 401/132–134; 604/1–3

(56) References Cited

U.S. PATENT DOCUMENTS

| 2,240,604 | A | * | 5/1941 | Berger | ............... | 401/134 |
|---|---|---|---|---|---|---|
| 3,481,676 | A | * | 12/1969 | Schwartzman | ............... | 401/134 |
| 4,507,111 | A | * | 3/1985 | Gordon et al. | ............... | 401/134 |
| 5,342,136 | A | * | 8/1994 | Fukami | ............... | 401/134 |
| 5,769,552 | A | | 6/1998 | Kelley | | |
| 5,791,801 | A | | 8/1998 | Miller | | |

OTHER PUBLICATIONS

Allegiance Healthcare Corporation, One-Step Fluid-Resistant Prep Solution, Allegiance a Cardinal Health Company, Copyright 2000, Allegiance Healthcare Corporation (Prevail-Fx is a trademark of Allegiance Healthcare Corporation).

* cited by examiner

*Primary Examiner*—David J. Walczak
(74) *Attorney, Agent, or Firm*—McKee, Voorhees & Sease, P.L.C.

(57) ABSTRACT

A liquid dispenser applicator for preoperative preparation of a target area of a patient's skin is comprised of two integrated components, a handle portion and a canister vessel. The two components are locked by a locking and sealing ring mechanism to prevent accidental rupture of the sterile antiseptic fluid in the canister vessel. When the lock is unlocked, the unit contains a perforator designed to initially slit the membrane followed by pushing it open further and thereafter venting it to provide dual-staged self-venting by the perforator for ease of flow.

12 Claims, 2 Drawing Sheets